United States Patent
Awaad et al.

(10) Patent No.: US 10,137,162 B1
(45) Date of Patent: Nov. 27, 2018

(54) **GASTROPROTECTIVE EXTRACTS OF *SONCHUS OLERACEUS* L.**

(71) Applicant: KING SAUD UNIVERSITY, Riyadh (SA)

(72) Inventors: Amani Shafeek Awaad, Al Kharj (SA); Shekhah Saud Almoqren, Riyadh (SA); Amal Ahmed Safhi, Riyadh (SA); Yara Mohamed Zain, Riyadh (SA); Reham Mostafa El-Meligy, Riyadh (SA); Fatmah Ali Al-Asamary, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/881,653

(22) Filed: Jan. 26, 2018

(51) Int. Cl.
*A61K 36/28* (2006.01)
*A61P 1/00* (2006.01)
*A61P 1/04* (2006.01)

(52) U.S. Cl.
CPC .............. *A61K 36/28* (2013.01); *A61P 1/00* (2018.01); *A61P 1/04* (2018.01); *A61K 2236/15* (2013.01); *A61K 2236/33* (2013.01); *A61K 2236/39* (2013.01); *A61K 2236/51* (2013.01)

(58) Field of Classification Search
CPC .................................................. A61K 36/28
See application file for complete search history.

(56) References Cited

U.S. PATENT DOCUMENTS

| | | | |
|---|---|---|---|
| 8,765,818 B1 | 7/2014 | Huang | |
| 9,125,912 B1 * | 9/2015 | Awaad | A61K 36/53 |
| 9,192,639 B1 * | 11/2015 | Awaad | A61K 36/39 |
| 9,533,019 B1 * | 1/2017 | Awaad | A61K 36/27 |
| 2016/0193265 A1 * | 7/2016 | Choi | A61K 36/185 |
| | | | 424/774 |

FOREIGN PATENT DOCUMENTS

| CN | 103536705 B | | 1/2014 |
|---|---|---|---|
| CN | 105326720 | * | 2/2016 |
| CN | 105343144 | * | 2/2016 |

OTHER PUBLICATIONS

3. Awaad, A. et al. Novel Compounds with New Antiulcergenic Activity from Convolvulus pilosellifolius Using Bio Guided Fractionation. Phytotherapy Research 2016. (Year: 2016).*
Ahmed A. Chemical Constituents of *Sonchus oleraceus* L. Egyptian J of Pharmaceutical Sciences 33(3-4)689-692, 1992. (Year: 1992).*
Awaad A. et al. Novel Compounds with New Anti-Ulcergenic Activity from Convolvulus pilosellfolius . . . Phytotherapy Research 1-5, 2016. (Year: 2016).*
Chu, H. et al. Extraction and Content Determination of Flavonoids in *Sonchus oleraceus* L. Anhui Nongye Kexue 40(24)12017-12019, 2012. (Year: 2012).*
El-Meligy, R.M. et al., "Prophylactic and Curative Anti-Ulcerogenic Activity and the Possible Mechanisms of Action of Some Desert Plants," Saudi Pharmaceutical Journal (25) pp. 387-396 (2017).
Xia, D. et al., "Antioxidant and Antibacterial Activity of Six Edible Wild Plants (*Sonchus* Spp.) in China," Natural Product Research (25)20 pp. 1893-1901 (2011).
Vilela, F.C. et al., "Anti-Inflammatory and Antipyretic Effects of Sonchus Oleraceus in Rats," Journal of Ethnopharmacology (127) pp. 737-741 (2010).
Jimoh, F.O. et al., "Comparison of the Nutritive Value, Antioxidant and Antibacterial Activities of Sonchus Asper and Sonchus Oleraceus," Rec. Nat. Prod. (5)1 pp. 29-42 (2011).
Awaad, A.S. et al., "Novel Compounds With New Anti-Ulcergenic Activity From Convolvulus Pilosellifolius Using Bio-Guided Fractionation," Phytother. Res. DOI:10.1002/ptr.5730 (2016).

* cited by examiner

*Primary Examiner* — Ralph J Gitomer
(74) *Attorney, Agent, or Firm* — Richard C. Litman

(57) ABSTRACT

The gastroprotective extracts of *S. oleraceus* L. are ethanol extracts (including the initial ethanol extract and serial extractions of the marc in ethanol), which are concentrated at low temperature to obtain a gummy residue that is dissolved in water. Lipoidal compounds are removed from aqueous extracts by filtration, and serial extracts proceeding from the aqueous extracts using chloroform to obtain low polarity phenolic compounds and n-butanol to obtain high polarity compounds and any remaining compounds. These extracts may be used to treat conditions of the stomach and colon including preventing peptic ulcers and treating ulcerative colitis.

3 Claims, No Drawings

GASTROPROTECTIVE EXTRACTS OF SONCHUS OLERACEUS L.

BACKGROUND

1. Field

The disclosure of the present patent application relates to treatment and prevention of gastrointestinal disorders, and particularly to gastroprotective extracts of Sonchus oleraceus L.

2. Description of the Related Art

The Asteraceae (commonly known as sunflowers) is a widespread family containing many genera. One Asteraceae species, Sonchus oleraceus L., has been traditionally used both as a food source and in treatment of gastrointestinal tract disorders. S. oleraceus L. contains a variety of phytochemical compounds, including sesqueterpene lactones, flavonoids, phenolic compounds, saponins, alkaloids, high concentrations of fatty acids, vitamin C, carotenoids, oxalic acid, and high mineral content. Analysis of S. oleraceus L. has identified numerous biological activities, including antioxidant, antidiabetic, anti-inflammatory, antipyretic, antinociceptive, anxiolytic, cytotoxic, and antibacterial activities.

Colitis is a disease characterized by inflammation of the inner lining of the colon. This inflammation may result from a number of causes, including infection, inflammatory bowel disease (Crohn's disease or ulcerative colitis), allergic reactions, radiation, and ischemia. Ulcerative colitis is a chronic inflammatory bowel disease characterized by inflammation and ulceration of the innermost lining of the bowel wall. While some pharmaceutical treatments are available for ulcerative colitis, as with all medications, some patients are prevented from using these drugs or would prefer to us an alternative due to undesirable side effects.

Peptic ulcers result from sores developing inside the lining of the stomach or the upper small intestine. Peptic ulcers may be caused by bacterial infection, long term use of common painkillers, or other medications (commonly when used in combination with an NSAID pain reliever). Patients at risk for peptic ulcers are often prescribed a preventative, such as an antacid.

Although many over-the-counter and prescription medications are available for treating these common conditions, none are completely effective. Thus, gastroprotective extracts of S. oleraceus L. solving the aforementioned problems are desired.

SUMMARY

The gastroprotective extracts of S. oleraceus L. may include total alcohol extracts. The gastroprotective extracts may further include lipoidal compounds removed from the total alcohol extracts by filtration, or serial extracts proceeding from the total alcohol extracts using chloroform and n-butane. These extracts may be used to treat conditions of the stomach and colon, including preventing peptic ulcers and treating ulcerative colitis.

These and other features of the present disclosure will become readily apparent upon further review of the following specification.

DETAILED DESCRIPTION OF THE PREFERRED EMBODIMENTS

The gastroprotective extracts of S. oleraceus L. may include total alcohol extracts. The gastroprotective extracts may further include lipoidal compounds removed from the total alcohol extracts by filtration, or serial extracts proceeding from the total alcohol extracts using chloroform and n-butane.

S. oleraceus L. aerial parts and roots may be harvested in Saudi Arabia, dried, ground to a powder, and extracted in ethanol. The resulting ethanol extracts may then be filtered, the filtrate being collected and saved and the marc being re-extracted four times in similar manner. The various ethanol filtrates are then combined (the aerial and root filtrates being kept separate) and concentrated, and the concentrated ethanol extracts are then mixed with hot water and filtered to separate lipoidal compounds from the aqueous extracts. The filtrate may then be serially extracted with chloroform and n-butane saturated with water. The resulting chloroform extracts include low polarity phenolic compounds, while the resulting n-butane extracts include high polarity phenolic and non-phenolic compounds.

These extracts may be used to treat disorders of the stomach and colon or protect against development of the disorders. For example, the extracts may be administered to assist in preventing the formation of ulcers, such as peptic ulcers. In a further embodiment, these extracts may be used to treat an inflammation of the bowel, such as ulcerative colitis.

As an extraction method, percolation is used to achieve complete extraction of desired constituents. Percolation allows a gravity driven flow of fresh, unsaturated solvent to flow through the source material. Percolation may be performed using any combination of equipment allowing for gravity driven extraction through a filter to progress over time. Percolation is typically performed using a percolating cone or "percolator", including an upper chamber for the filter, extraction substrate, and solvent, and a lower chamber to collect the extract solution. Alternatively, percolation may be performed using a Soxhlet extractor.

Another extraction method that may be used is serial exhaustive extraction. Serial exhaustive extraction is commonly used to separate different phytochemical groups from a crude extract. Serial extraction commonly employs solvents with different polarities to enhance isolation of compounds from crude extracts. If the crude extract is performed in ethanol, followed by extraction in hot water to remove lipoidal compounds, serial extraction may be performed first using chloroform, followed by n-butanol. In the alternative, serial extraction may proceed from hexane, to acetone, to methanol; from hexane, to ethyl acetate, to acetone, to methanol; or through any other progression of appropriate solvents. The solvents selected may be based upon particular polarities desired to be separated at each step of the extraction process to enhance the concentration of a particular class or type of compounds found in the final extract.

Example 1

S. Oleraceus L. Aerial Parts Extraction

S. oleraceus L. aerial parts were freshly harvested from Al-Dhelam (south of Riyadh, KSA) Alkharj in Saudi Arabia, washed (to remove sand or dust), and dried using a hot air steam drying machine. The plant materials were spread out on shallow trays which were placed on mobile racks and passed into a tunnel where they meet a stream of warm air using constant temperature at about 20-40° C. The dried plant materials were then ground to powder.

A sample of 500 g of powdered S. oleraceus L. aerial parts were extracted by percolation in 2 liters of aqueous ethanol (95%) for about 2 days at room temperature. The solvent was filtered over filter paper and the marc was collected and extracted a further four times by repetition of the extraction and filtration steps.

The total alcohol extracts from all five extractions were mixed and concentrated using a rotatory evaporator at a temperature not exceeding 25° C. This process produced about 99 g of gummy residue.

The gummy residue was dissolved in deionized water (about 400 ml) and filtered using MicroFunnel™ Filter Funnels with the aid of a suction pump. The filtered aqueous extract (the filtrate) was collected and the lipoidal compounds trapped on the filter were dissolved in distilled water and re-filtered to remove any remaining soluble compounds. The non-filtered lipoidal compound containing residue (about 15 g) trapped on the filter was retained for further testing ("SAL" extract).

A portion of the filtered aqueous extract was set aside for further testing ("SA" extract). The remaining filtered aqueous extract was then extracted to exhaustion using chloroform (analytical grade). The collected chloroform extracts were filtered over anhydrous sodium sulfate to remove any trace of water. The chloroform extracts were then dried using reduced pressure at a temperature not exceeding 20° C. to obtain low polarity phenolic extracts (including flavonoids and Coumarin) with a weight of about 4.9 g ("CSA" extract).

After removal of the low polarity phenolic compounds, the aqueous extract was extracted to exhaustion using n-butanol (saturated with water). The n-butanol extracts were filtered oved anhydrous sodium sulfate to remove any trace of water. The n-butanol extracts were then dried using reduced pressure at a temperature not exceeding 35° C., to obtain highly polar phenolic and non-phenolic compounds (including carbohydrates and/or glycosides, flavonoids, protein and/or amino acids, phenolic compounds and tannins) with a weight of about 14.5 g ("BSA" extract).

Example 2

S. oleraceus L. Root Parts Extraction

S. oleraceus L. root parts were freshly collected from Al-Dhelam (south of Riyadh. KSA) Alkharj in Saudi Arabia, washed (to remove sand or dust), and dried using a hot air steam drying machine. The plant materials were spread out on shallow trays which were placed on mobile racks and passed into a tunnel where they meet a stream of warm air using constant temperature at about 50-55° C. The dried plant materials were then ground to powder.

A sample of 500 g of S. oleraceus L. root parts were extracted by percolation in 2 liters of aqueous ethanol (95%) for about 2 days at room temperature. The solvent was filtered over filter paper and the marc was collected and extracted a further four times by repetition of the extraction and filtration steps.

The total alcohol extracts from all five extractions were mixed and concentrated using a rotatory evaporator at a temperature not exceeding 25° C. This process produced about 45.5 g of gummy residue.

The gummy residue (about 45.5 g) was dissolved in deionized water (about 200 ml) and filtered using Micro-Funnel™ Filter Funnels with the aid of a suction pump. The filtered aqueous extract was collected and the lipoidal compounds trapped on the filter were dissolved in distilled water and re-filtered to remove any remaining soluble compounds. The non-filtered lipoidal compound-containing residue (5.5 g) trapped on the filter was retained for further testing ("SRL" extract).

A portion of the filtered aqueous extract was set aside for further testing ("SR" extract). The remaining filtered aqueous extract was then extracted to exhaustion using chloroform (analytical grade). The collected chloroform extracts were filtered over anhydrous sodium sulfate to remove any trace water. The chloroform extracts were then dried using reduced pressure at a temperature not exceeding 20° C., to obtain low polarity phenolic extracts (including flavonoids and Coumarin) with a weight of 4.5 g ("CSR" extract).

After removal of low polarity phenolic compounds, the aqueous extract was extracted to exhaustion using n-butanol (saturated with water). The n-butanol extracts were filtered oved anhydrous sodium sulfate to remove any trace of water. The n-butanol extracts were then dried using reduced pressure at a temperature not exceeding about 35° C., to obtain highly polar phenolic and non-phenolic compounds (including carbohydrates and/or glycosides, flavonoids, protein and/or amino acids, phenolic compounds and tannins) with a weight of 15.3 g ("BSR" extract).

Example 3

Extract Safety Testing

Phytochemical screening of S. oleraceus L. total alcohol extracts (SA, SR) confirmed the presence of: carbohydrates and/or glycosides, flavonoids, sterols and/or triterpenes, protein and/or amino acids, phenolic compounds and tannins and the absence of saponin, anthraquinones, alkaloids, and cardenolides.

Swiss albino mice of both sex (26-30 g) and male Wistar rats (180-200 g) were housed in standard polypropylene cages with wire mesh tops and maintained under standard conditions (temperature 23±1.0° C., humidity 55±10%, 12 h light/12 h dark cycle). They were fed a standard pellet diet with water ad libitum and were allowed to adapt to the laboratory environment for one week before experimentation.

Dried plant extracts obtained using the method of Example 1 (SA, SR, SAL, SRL, CSA, CSR, BSA & BSR) were suspended in distilled water just before administration (for each experiment) by the aid of few drops of Tween 80.

The oral median lethal dose ($LD_{50}$) of each alcohol extract of S. oleraceus L. parts (SA & SR) was separately determined by dosing mice with up to about 5000 mg/kg. The extracts are characterized by a low degree of toxicity. Doses of each alcohol extract did not produce any symptoms of acute toxicity. None of the mice died during 24 hours of further observation. Thus, the extracts are considered safe for humans.

Alcohol extracts of S. oleraceus L. aerial and root parts (SA & SR) were administered orally daily for 14 consecutive days at a dose of about 500 mg/kg to male Wistar rats. Liver functions were evaluated by measuring the serum activity of ALT and AST in addition to serum levels of total bilirubin, total proteins and albumin. Serum concentrations of urea and creatinine were determined calorimetrically as measures of kidney functions. No alteration of liver or kidney functions was observed (Table 1). All values were expressed as mean±S.D. Comparisons between means were carried out using a one-way ANOVA test followed by the Tukey HSD test using SPSS, version 14 (SPSS, Chicago, Ill.). Differences at $p<0.05$ were considered statistically significant.

TABLE 1

Effect of SA & SR Extracts on Liver and Kidney Function (500 mg/kg)

|  | ALT (U/L) | AST (U/L) | Total Bilirubin (mg/dL) | Total Protein (g/dL) | Albumin (g/dL) | Urea (mg/dL) | Creatinine (mg/dL) |
|---|---|---|---|---|---|---|---|
| Control | 59.33 ± 1.2 | 49.40 ± 1.5 | 1.57 ± 0.1 | 8.56 ± 0.4 | 3.9 ± 0.2 | 36.11 ± 0.1 | 0.51 ± 0.1 |
| Aerial parts (SA) | 61.51 ± 1.1 | 47.10 ± 1.2 | 1.60 ± 0.2 | 7.90 ± 0.1 | 3.3 ± 0.1 | 36.78 ± 0.2 | 0.52 ± 0.1 |
| Root (SR) | 58.10 ± 1.4 | 58.10 ± 1.1 | 1.58 ± 0.4 | 8.25 ± 0.3 | 3.8 ± 0.4 | 35.93 ± 0.2 | 0.49 ± 0.3 |

Example 3

Gastroprotective Testing

The absolute ethanol-induced ulcer model was used for evaluation of gastroprotective activity. Groups of 6 Male Wistar rats were used. Treated groups received either total alcohol extracts (SA or SR) at doses of about 250 mg/kg or about 500 mg/kg. Successive extracts (SAL, SRL, CSA, CSR, BSA & BSR) were administered at doses of about 150 mg/kg. A treatment group received Omeprazole (about 20 mg/kg) and a control group received water (about 5 mL/kg). All treatments were administered orally to all groups. Thirty minutes later, all groups were orally administrated absolute ethanol (about 1 mL/200 g body weight). After one hour all rats were sacrificed, the stomachs were rapidly removed, opened along their greater curvature, and gently rinsed under running tap water.

The number and severity of ulcers were visually counted and the ulcer index was calculated. Ulcer indices (mm) were calculated as the sum of the total length of long ulcers and petechial lesions in each group of rats divided by its number. Percent protection was determined according to the following formula:

$$\% \text{ Protection of Test Group} = \left(\text{Control Ulcer Index} - \frac{\text{Test Group Ulcer Index}}{\text{Control Ulcer Index}}\right) \times 100$$

All values were expressed as mean+S.D. Comparisons between means were carried out using a one-way ANOVA test followed by the Tukey HSD test using SPSS, version 14 (SPSS, Chicago, Ill.). Differences at p<0.05 were considered statistically significant.

The root extract of S. oleraceus L. showed promising gastroprotective activity (Table 2). Treatment with total alcohol extract of the root (SR) at 500 mg/kg produced 88.5% protection, significantly more protection than afforded by 20 mg/kg omeprazole (45.83%). The butanol root extract (BSR) also produced significant protection (76.66%). The aerial parts total extract SA showed more limited gastroprotective activity in both tested doses (250 and 500 mg/kg), producing 25% and 28.33% protection respectively. The butanol aerial parts extract showed more promising activity (54.16% protection). All tested extracts demonstrated some degree of protection. These results suggest that the phenolic contents of the butanol extracts of both the aerial parts and the roots might play an important role in gastroprotective activity.

TABLE 2

Gastroprotective Activity of S. oleraceus L Extracts

|  | Dose mg/kg | Score | No. of ulcers | Ulcer Index | % Protection |
|---|---|---|---|---|---|
| Control |  | 4.50 | 15.00 ± 0.24 | 12.00 ± 0.94 | 0.00 |
| Omeprazole | 20 | 2.50 | 7.60* ± 0.65 | 6.50* ± 0.24 | 45.83 |
| SA | 250 | 3.50 | 8.80* ± 0.51 | 9.00 ± 0.41 | 25.00 |
| SA | 500 | 3.00 | 8.30* ± 0.35 | 8.60* ± 0.51 | 28.33 |
| SAL | 150 | 4.00 | 9.60 ± 0.95 | 10.20 ± 0.77 | 15.00 |
| CSA | 150 | 3.00 | 6.80* ± 1.92 | 8.50 ± 0.51 | 28.30 |
| BSA | 150 | 2.00 | 4.40* ± 0.55 | 5.50* ± 0.41 | 54.16 |
| SR | 250 | 1.80 | 4.80* ± 0.11 | 5.20* ± 0.90 | 56.66 |
| SR | 500 | 1.00 | 3.50* ± 0.38 | 1.38* ± 0.58 | 88.50 |
| SRL | 150 | 3.00 | 8.60* ± 0.95 | 9.20 ± 0.77 | 23.33 |
| CSR | 150 | 2.00 | 4.80* ± 0.11 | 5.20* ± 0.90 | 56.66 |
| BSR | 150 | 1.50 | 4.00* ± 0.17 | 2.80* ± 0.82 | 76.66 |

*= Significantly different from control ulcer at p < 0.05.

Example 4

Ulcerative Colitis Treatment

Groups of 6 Male Wistar rats were used. Rats of groups 1 and 2 received the vehicle (5 mL/kg) and served as normal control and control colitis groups respectively. The third group was administered dexamethasone (0.1 mg/kg) and served as a reference group. Rats of groups 4-10 received about 250 & 500 mg/kg of total alcohol extracts (SA & SR) and successive extracts (SAL, SRL, CSA, CSR, BSA & BSR), at doses of about 150 mg/kg. All medications were administered orally, once daily for 5 consecutive days and the first dose was administered about 2 h after ulcerative colitis induction by about 2 mL (4%, v/v) acetic acid in saline. Ulcer indices (mm) were calculated as the sum of the total length of long ulcers and petechial lesions in each group of rats divided by its number.

All values were expressed as mean+S.D. Comparisons between means were carried out using a one-way ANOVA test followed by the Tukey HSD test using SPSS, version 14 (SPSS, Chicago, Ill.). Differences at p<0.05 were considered statistically significant.

Control colitis rats showed lesion score, ulcer area, ulcer index and Wet W/L (g/cm) values of 4.50±0.49, 29.21±1.22, 35.21±1.82 and 0.99±0.21, respectively (Table 3). Increase of the wet weight/length of the colon specimens is considered an indicator of inflammation. These inflammatory indices were significantly improved by oral dosing of dexamethasone for 5 days after colitis induction. Among the investigated extracts of S. oleraceus L.; the total extract of the aerial parts (SA) at 500 mg/kg showed a strong anti-ulcerative colitis activity. This activity was similarly observed for the butanol (BSA) and chloroform (CSA) extracts of the aerial parts (Table 3). All tested extracts demonstrated some degree of protection. These results suggest that the phenolic contents of the butanol extracts might play an important role in gastroprotective activity.

TABLE 3

Effect of Extracts on Ulcerative Colitis

|  | Dose | Lesion score (0-5) | Ulcer area (mm$^2$) | Ulcer index | Wet W/L (g/cm) | % protection |
| --- | --- | --- | --- | --- | --- | --- |
| Control | 5 mL/kg | 0.00 ± 0.00 | 0.00 ± 0.00 | 0.00 ± 0.00 | 0.38 ± 0.05 | — |
| Colitis | 5 mL/kg | 4.50 ± 0.49 | 29.21 ± 1.22 | 35.21 ± 1.82 | 0.95 ± 0.21 | — |
| Dexamethasone | 0.1 mg/kg | 1.50* ± 0.25 | 11.70* ± 1.17 | 12.90* ± 1.03 | 0.52* ± 0.12 | 66.36 |
| SA | 250 mg/kg | 3.00* ± 0.14 | 21.4* ± 0.27 | 28.20* ± 0.39 | 0.69* ± 0.14 | 19.90 |
| SA | 500 mg/kg | 1.50* ± 0.15 | 9.30* ± 0.27 | 8.00* ± 0.34 | 0.40* ± 0.15 | 77.28 |
| SAL | 150 mg/kg | 3.50 ± 0.13 | 23.00 ± 0.30 | 29.50 ± 0.43 | 0.86 ± 0.05 | 16.21 |
| CSA | 150 mg/kg | 3.00* ± 0.16 | 22.2* ± 0.17 | 18.42* ± 0.29 | 0.60* ± 0.02 | 47.68 |
| BSA | 150 mg/kg | 2.00* ± 0.17 | 11.00* ± 0.07 | 15.00* ± 0.12 | 0.46* ± 0.11 | 57.40 |
| SR | 250 mg/kg | 4.00 ± 0.22 | 23.97 ± 0.20 | 30.10 ± 0.40 | 0.85 ± 0.06 | 14.51 |
| SR | 500 mg/kg | 3.00* ± 0.34 | 19.45* ± 0.20 | 23.22* ± 0.15 | 0.62* ± 0.40 | 34.05 |
| SRL | 150 mg/kg | 4.00 ± 0.12 | 25.00 ± 0.17 | 29.80 ± 0.22 | 0.80 ± 0.01 | 15.36 |
| CSR | 150 mg/kg | 3.00* ± 0.21 | 18.15* ± 0.57 | 27.12* ± 0.19 | 0.65* ± 0.04 | 22.98 |
| BSR | 150 mg/kg | 3.00* ± 0.14 | 20.50* ± 0.53 | 27.50* ± 0.27 | 0.62* ± 0.05 | 21.90 |

*Significantly different from control colitis at p <0.05.

It is to be understood that the gastroprotective extracts of S. oleraceus L are not limited to the specific embodiments described above, but encompass any and all embodiments within the scope of the generic language of the following claims enabled by the embodiments described herein, or otherwise described above in terms sufficient to enable one of ordinary skill in the art to make and use the claimed subject matter.

We claim:

1. A method of producing gastroprotective extracts of Sonchus (S.) oleraceus L., comprising the steps of:
   selecting a source material consisting of S. oleraceus L. roots;
   grinding the source material into a powder to produce 500 grams of powder;
   extracting the powder by percolation in 2 liters of 95% aqueous ethanol for 2 days at room temperature to produce an ethanol extract;
   concentrating the ethanol extract in a rotary evaporator at a temperature of less than 25° C. to form a residue;
   suspending the residue in distilled water until it is dissolved;
   filtering the dissolved residue to produce an aqueous filtrate;
   collecting any lipoidal matter trapped on a filter;
   further extracting a portion of the aqueous filtrate to exhaustion in chloroform;
   drying the chloroform extracts at a temperature less than 20° C.;
   further extracting the aqueous filtrate to exhaustion with n-butanol; and
   drying the n-butanol extracts at a temperature less than 35° C.; recovering the gastroprotective extracts of S. oleraceus L.

2. The method of producing gastroprotective extracts of Sonchus oleraceus L. according to claim 1, wherein the S oleraceus L source material is harvested from Al-Dhelam in Saudi Arabia.

3. The method of producing gastroprotective extracts of Sonchus oleraceus L. according to claim 1, further comprising the steps of:
   filtering the ethanol extract with filter paper to obtain filtrate and marc;
   collecting the filtrate;
   extracting the marc left by the filtering step by percolating in ethanol to obtain additional ethanol extract;
   repeating the filtering, collecting, and extracting the marc steps on the additional ethanol extract three additional times to collect four filtrates of ethanol extract; and
   combining the four filtrates of ethanol extract prior to said step of concentrating the ethanol extract.

* * * * *